Figure 1:
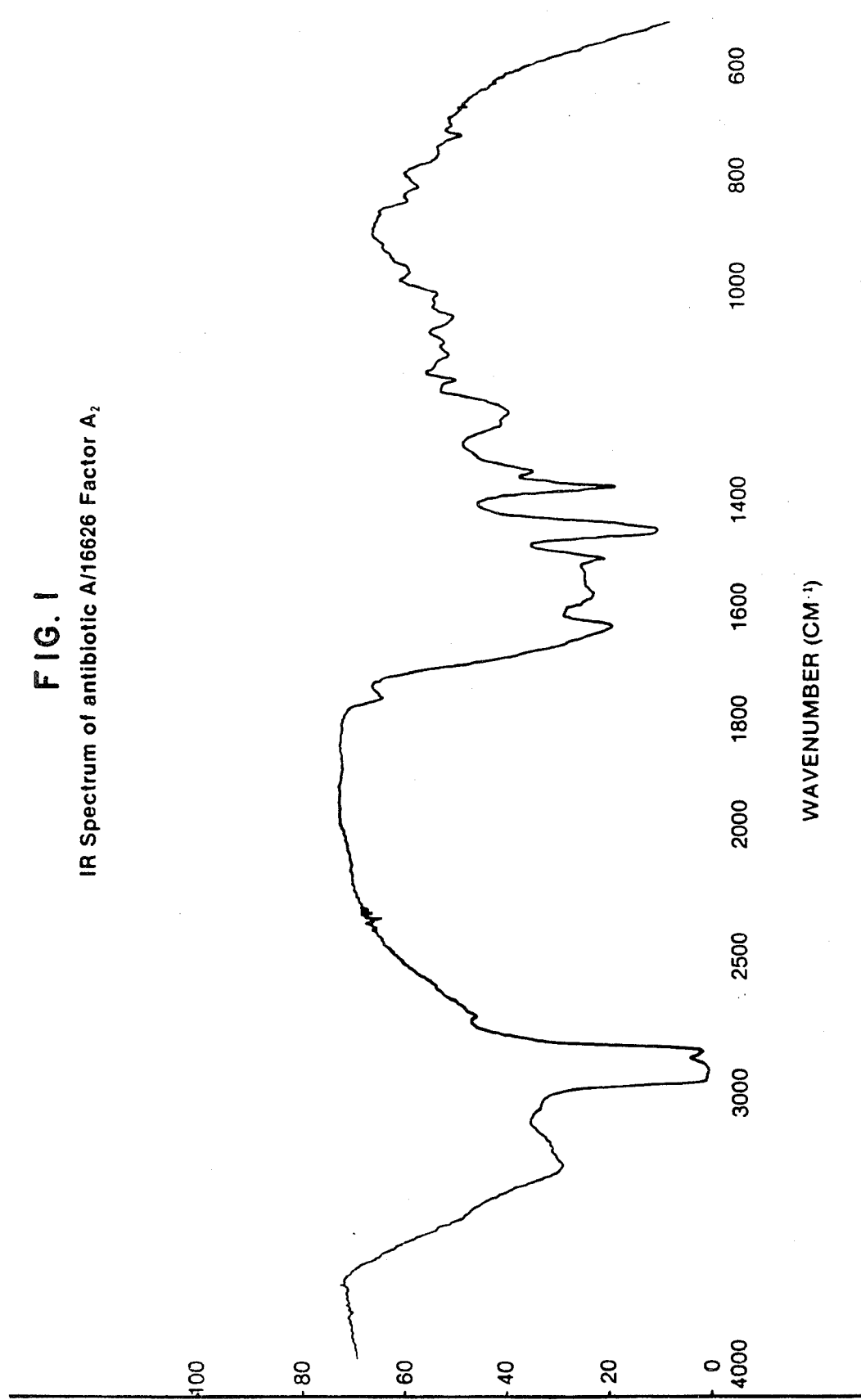

United States Patent [19]

Cavalleri et al.

[11] 4,427,656

[45] Jan. 24, 1984

[54] ANTIBIOTIC A/16686 FACTOR A2, THE PROCESS FOR THE PREPARATION THEREOF AND THE CO-PRODUCED ANTIBIOTIC A/16686 FACTORS A1 AND A3

[75] Inventors: Bruno Cavalleri, Milan; Enrico Selva, Gropello Cairoli (PV), both of Italy

[73] Assignee: Gruppo Lepetit S.p.A., Milan, Italy

[21] Appl. No.: 288,718

[22] Filed: Jul. 31, 1981

[30] Foreign Application Priority Data

Aug. 16, 1980 [GB] United Kingdom ............... 8026758

[51] Int. Cl.³ .................. A61K 35/00; C12P 1/06; C12R 1/45
[52] U.S. Cl. ................................... 424/118; 435/169; 435/827
[58] Field of Search .............. 435/68, 72, 132, 128, 435/253, 827, 155, 169; 424/118

[56] References Cited

U.S. PATENT DOCUMENTS

| | | | |
|---|---|---|---|
| 3,780,174 | 12/1973 | Hamill et al. | 424/118 |
| 3,824,305 | 7/1974 | Hamill et al. | 424/118 |
| 4,239,751 | 12/1980 | Coronelli et al. | 435/169 |
| 4,303,646 | 12/1981 | Cavalleri et al. | 424/118 |
| 4,328,316 | 5/1982 | Cavalleri et al. | 435/253 |

*Primary Examiner*—Robert J. Warden
*Assistant Examiner*—John E. Tarcza
*Attorney, Agent, or Firm*—William J. Stein; Raymond A. McDonald; John J. Kolano

[57] ABSTRACT

The present invention refers to a chlorine containing antibiotic substance, named antibiotic A/16686 factor $A_2$, in an essentially pure form. The invention also relates to the process for the production of antibiotic A/16686 factors $A_2$ by cultivation of an Actinoplanes strain and to the co-produced antibiotic A/16686 factos $A_1$ and $A_3$. Antibiotic A/16686 factors $A_1$, $A_2$ and $A_3$ as well as the corresponding non-toxic physiologically acceptable acid addition salts are antimicrobial agents particularly active against gram-positive bacteria.

8 Claims, 7 Drawing Figures

U.V. Spectrum of antibiotic A/16686 factor $A_2$

1H-NMR Spectrum of antibiotic A/16686 Factor A₂

IR Spectrum of antibiotic A/16686 Factor $A_1$

U.V. Spectrum of antibiotic A/16686 factor $A_1$

IR Spectrum of antibiotic A/16686 Factor $A_3$

U.V. Spectrum of antibiotic A/16686 factor $A_3$

ANTIBIOTIC A/16686 FACTOR $A_2$, THE PROCESS FOR THE PREPARATION THEREOF AND THE CO-PRODUCED ANTIBIOTIC A/16686 FACTORS $A_1$ AND $A_3$

The present invention relates to an antibiotic substance arbitrarily designated as antibiotic A/16686 factor $A_2$, to the process for the preparation thereof and to the co-produced antibiotic A/16686 factors $A_1$ and $A_3$.

The first object of the present invention is antibiotic A/16686 factor $A_2$, a chlorine containing antibiotic substance, in an essentially pure form.

This antibiotic substance is produced by culturing a hitherto undescribed strain which has been characterized taxonomically as a novel species of the Actinoplanes genus.

A culture of this strain, which was isolated from a soil sample collected at Vaghalbod (India), has been deposited on Jan. 30, 1979 with the permanent culture collection of ATCC (American Type Culture Collection—12301 Parklawn Drive, Rockville—Md. 20852—U.S.), where it has been accorded the accession number ATCC 33076.

Besides antibiotic A/16686 factor $A_2$ which is the major factor produced by this culture, other two minor individual antibiotic factors have been isolated and separated from a fermentation broth produced by the new Actinoplanes culture. These individual antibiotics are arbitrarily designated as antibiotic A/16686 factors $A_1$ and $A_3$. Antibiotic A/16686 factor $A_2$ is produced by culturing the strain Actinoplanes sp. ATCC 33076 under submerged aerobic fermentation conditions until a substantial level of antibiotic activity is produced. Antibiotic A/16686 factor $A_2$ is recovered as an antibiotic complex with factors $A_1$ and $A_3$ by extraction of both the broth and the mycelium with polar organic solvents, and is then separated from the A/16686 complex and isolated as an essentially pure individual antibiotic compound by chromatographic techniques such as HPLC, column chromatography and preparative thin layer chromatography. The same techniques are also useful for separating the co-produced factors $A_1$ and $A_3$.

Antibiotic A/16686 factor $A_2$, as well as the co-produced factors $A_1$ and $A_3$, have a basic character and are therefore capable of forming acid addition salts. It is intended that physiologically acceptable acid addition salts of antibiotic A/16686 factor $A_2$, as well as those of antibiotic A/16686 factors $A_1$ and $A_3$, are part of the present invention.

"Physiologically-acceptable" acid addition salts are salts which are also pharmaceutically acceptable, that is, salts in which the toxicity of the compound as a whole is not increased relative to the non-salt form. Representative and suitable acid addition salts include the addition salts with organic or inorganic acids such as hydrochloric, hydrobromic, sulfuric, phosphoric, nitric, tartaric, acetic, succinic, lactic, glutamic, methanesulfonic and the like acids.

A/16686 factors $A_1$, $A_2$, and $A_3$ free bases can be prepared from the corresponding acid addition salts, or viceversa A/16686 factor $A_1$, $A_2$, and $A_3$ as acid addition salts can be prepared from the corresponding free bases, according to procedures commonly employed in this field. The free bases of antibiotic A/16686 factor $A_1$, $A_2$, and $A_3$ are obtained from the corresponding acid addition salts, for instance, by treatment of a solution of the acid addition salt with barium hydroxide while the reaction of the free bases with the selected oganic or inorganic acid in an inert solvent solution affords the corresponding acid addition salts.

For simplicity in discussions of utility, the term A/16686 compound is used herein to refer to a compound selected from the group consisting of A/16686 factors $A_1$, $A_2$, and $A_3$ and the corresponding non-toxic physiologically acceptable acid addition salts.

The A/16686 compounds inhibit in vitro the growth of certain pathogenic bacteria, especially gram-positive; moreover parenteral administration of A/16686 compounds gives a high degree of protection against experimental infections in mice. In addition the A/16686 compounds are useful in the prevention and treatment of dental caries.

As stated above, antibiotics A/16686 are produced by culturing a novel strain of the Actinoplanes genus named Actinoplanes sp. ATCC 33076.

The characteristics of this strain are given in the following paragraphs.

Morphology

The strain grows well on different media with an orange color of the substrate mycelium. It does not produce pigment. Aerial mycelium is always absent. At microscopic examination the vegetative mycelium reveals branched hyphae with a diameter of about 1 $\mu$m. The sporangia form scantly only on potato-agar and are globose with a very irregular surface and a diameter ranging from 5.0 to 9.0 $\mu$m. Sporangial release is observed after rupture of the wall of the sporangium. The subspherical spores are motile (1.0–1.5 $\mu$m diameter). Analysis of the cell-wall components reveals meso-diaminopimelic acid and sugar pattern of type D (Lechevalier et al.—Chemical composition as a criterium in the classification of Actinomycetes. Adv. Applied Microbiology, 14, 1971. Academic Press, N.Y.).

Cultural characteristics

Table 1 reports the culture characteristics of Actinoplanes ATCC 33076 cultivated on various standard media suggested by Shirling and Gottlieb (Intern. J. System. Bact. 16, 313–340, 1966) and other media recommended by Waksman (The Actinomycetes, Vol. II—The Williams and Wilkins Co. 1961). The cultural characteristics were determined after 6 to 14 days of incubation at 30° C.

TABLE I

Cultural characteristics
The number of some of the culture media refers to those given by Shirling and Gottlieb in Methods for characterization of Streptomyces species - Intern. J. System. Bact. 16, 313–340, 1966.

| Culture media | Culture characteristics |
|---|---|
| Medium No. 2 (yeast extract-malt agar) | Abundant growth, wrinkled surface, light brown 12 H 12 |
| Medium No. 3 (oatmeal agar) | Scant growth, thin, light orange 9 B 6 |
| Medium No. 4 (inorganic salts-starch agar) | Moderate growth, crusty surface, orange 11 L 12 |
| Medium No. 5 (glycerol-asparagine agar) | Scant growth, hyaline |
| Medium No. 6 (peptone-yeast extract-iron agar) | Scant growth, hyaline to light brown |
| Medium No. 7 (tyrosine agar) | Scant growth, smooth surface, brown 6 D 11 |
| Oatmeal agar (according to Waksman) | Abundant growth, wrinkled surface, orange to brown |

TABLE I-continued

Cultural characteristics
The number of some of the culture media refers to those given by Shirling and Gottlieb in Methods for characterization of Streptomyces species - Intern. J. System. Bact. 16, 313-340, 1966.

| Culture media | Culture characteristics |
| --- | --- |
| Hickey and Tresner's agar | 12 C 10<br>Abundant growth, crustly surface, orange 11 G 8 |
| Czapeck glucose agar | Moderate growth, crusty surface, orange 11 G 8 |
| Glucose asparagine agar | Scant growth, crusty surface light orange 11 F 6 |
| Nutrient agar | Moderate growth, smooth surface, orange 11 G 8 |
| Potato agar | Abundant growth, wrinkled surface, amber-brown 12 E 10 |
| Bennett's agar | Abundant growth, wrinkled surface, orange 11 G 8 |
| Calcium malate agar | Moderate growth, smooth surface, light orange 10 C 6 |
| Skim milk agar | Abundant growth, wrinkled surface, orange 9 L 2 |
| Czapeck agar | Moderate growth, crusty surface, orange 10 D 7 |
| Egg agar | Moderate growth, smooth surface, hyaline to light orange |
| Peptone glucose agar | Abundant growth, wrinkled surface, orange 11 G 11 |
| Agar | Very scant growth, smooth surface, hyaline |
| Loeffler serum | Very scant growth, smooth surface, orange |
| Potato | Scant growth, crusty, light brown |
| Gelatin | Scant growth, light orange |
| Cellulose | Very scant growth, thin, hyaline |

Letters and numbers refer to the color determined according to Maerz and Paul - A dictionary of color -McGraw Hill Inc., New York, 1950

Carbon utilization

Table II reports the utilization of carbon sources examined according to the method of Pridham and Gottlieb (J. Bact. 56, 107, 1948).

TABLE II

| Carbon sources | Utilization |
| --- | --- |
| Inositol | − |
| Fructose | + |
| Rhammose | + |
| Mannitol | − |
| Xylose | + |
| Raffinose | − |
| Arabinose | + |
| Cellulose | − |
| Sucrose | + |
| Glucose | + |
| Mannose | + |
| Lactose | − |
| Salicin | + |

+ = positive utilization
− = no growth

Physiological characteristics

Table III reports the physiological characteristics of the strain.

TABLE III

| Test | Results |
| --- | --- |
| Hydrolysis of starch | positive |
| $H_2S$ formation | positive |
| Tyrosine reaction | negative |
| Casein hydrolysis | positive |
| Solubilization of calcium malate | negative |
| Liquefaction of gelatine | positive |
| Litmus milk — coagulation | positive |
| Litmus milk — peptonization | negative |
| Cellulose decomposition | negative |

As in the case with other organisms, the characteristics of the A/16686 factor $A_2$ producing strain Actinoplanes sp. ATCC 33076, are subject to variation. For example, artificial variants and mutants of the ATCC 33076 strain may be obtained by treatment with various known mutagens such as ultraviolet rays, X rays, high-frequency waves, radioactive rays and chemicals. All natural and artificial variants and mutants which belong to this Actinoplanes species and produce antibiotic A/16686 factor $A_2$ may be used in this invention.

For producing the A/16686 antibiotics the strain Actinoplanes sp. ATCC 33076 is cultivated under aerobic conditions in an aqueous nutrient medium containing an assimilable source of carbon, an assimilable source of nitrogen and inorganic salts. Said culture medium can be any one of a number of nutrient media usually employed in the fermentation art, however certain media are preferred. Thus, for instance, preferred carbon sources are glucose, fructose, mannose, sucrose and the like in various grades of purity. Preferred nitrogen sources are soybean meal, peptone, meat extract, yeast extract, tryptone, amino acids and the like. Among the inorganic salts which can be incorporated in the culture media are the customary soluble salts capable of yielding sodium, potassium, iron, zinc, cobalt, magnesium, calcium, ammonium, chloride, carbonate, sulfate, nitrate and like ions. Ordinarily the antibiotic-producing strain is precultured in a shake flask, then the culture is used to inoculate jar fermentors for production of substantial quantities of the A/16686 antibiotics. The medium used for the preculture can be the same as that employed for larger fermentations, but other media can also be employed.

The A/16686-producing strain can be grown at temperatures between about 20° C. and about 37° C. and preferably at temperatures of about 28°–30° C.

During the fermentation, antibiotic production can be followed be testing samples of the broth or of extracts of the mycelial solids for antibiotic activity.

Organisms known to be sensitive to the A/16686 antibiotics are useful for this purpose. One especially useful assay organism is Sarcina lutea ATCC 9341. The bioassay is conveniently performed by the agar diffusion method on agar plates. Maximum production of antibiotic activity generally occurs between about the third and the fifth days. The antibiotics produced during fermentation of the strain Actinoplanes sp. ATCC 33076 are found mainly in the mycelial mass. A preferred method of recovering the A/16686 antibiotics is, therefore, by extraction of the separated mycelium.

Extraction of the mycelial mass is best accomplished with methanol, but other lower alkanols and acetone are also suitable. The A/16686 antibiotics are recovered from the extracting solvent by routine procedure to give a mixture of the A/16686 antibiotics, the A/16686 complex. The A/16686 complex is further purified, and then the individual factors are separated from each other. Separation of the A/16686 complex into the single components may be achieved by a variety of recognized methods which essentially involve chromatographic procedures. For optimum separation of factors, reverse phase HPLC is preferred. In such HPLC separation, a preferred column is μ-Bondapack ®C$_{18}$, trademark of Waters Company, and preferred mobile phases are mixtures of aqueous HCOONH$_4$ and CH$_3$CN in variable ratios. For large scale separation of antibiotic A/16686 factor A$_2$ column chromatography is preferably employed. In such column separation a preferred adsorbent is Amberlite®XAD, trademark of Rohm and Hass Co., and preferred solvent systems are mixtures of water and acetonitrile and mixtures of ammonium formiate and acetonitrile. Separation of minor factors A$_1$ and A$_3$ by column chromatography may be carried out but it requires subsequent column separation of enriched fractions. Again Amberlite XAD ®, trademark of Rohm and Hass Co., is a preferred adsorbent and mixtures of water and acetonitrile and mixture of ammonium formiate and acetonitrile are the preferred solvent systems.

A/16686 Factor A$_2$

A/16686 factor A$_2$ is a white amorphous powder which melts with decomposition at about 210°-220° C.

A/16686 factor A$_2$ is soluble in water, dimethylformamide, aqueous methanol, 0.1 N HCl; it is poorly soluble in absolute ethanol and in n-butanol; it precipitates from the aqueous solution by the addition of a solution saturated with NaHCO$_3$.

Elemental analysis of A/16686 factor A$_2$ previously dried at about 140° C. under inert atmosphere indicates the following approximate percentage composition (average); carbon, 54.57%, hydrogen, 6.19%, nitrogen, 10.88%.

Chlorine analysis gives the following percentage: chlorine 1.37%. The infrared adsorption spectrum of A/16686 factor A$_2$ in nujol is shown in FIG. 1 of the accompanying drawings. The following absorption maxima are observed: 3290, 2930 and 2860 (nujol), 1765, 1635, 1510, 1455 and 1375 (nujol), 1240, 1175, 1130, 1060, 1015, 975, 840 and 815 cm$^{-1}$.

Figure 2:
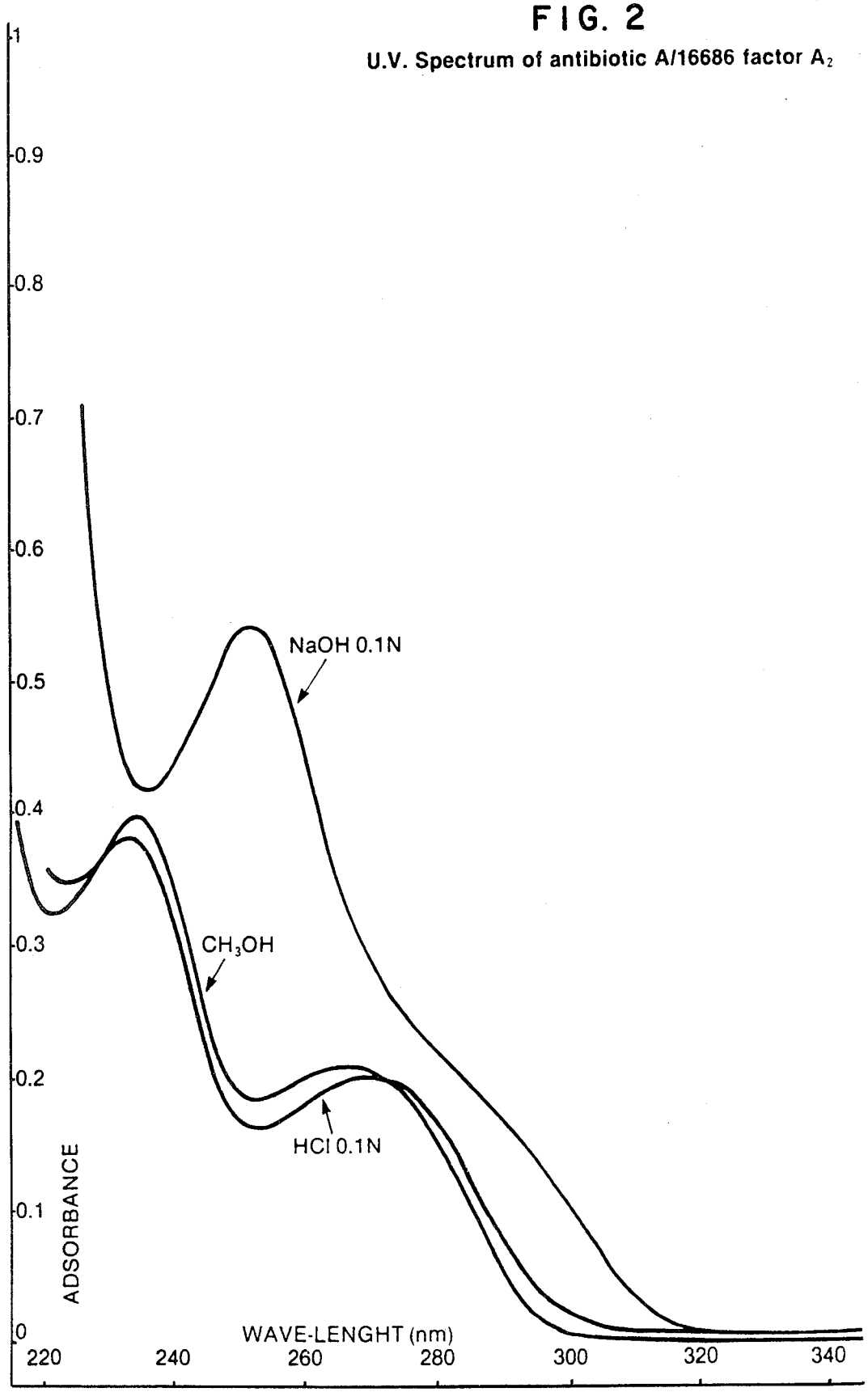

The ultraviolet absorption spectrum of A/16686 factor A$_2$, which is given in FIG. 2 of the accompanying drawings, exhibits the following absorption maxima:

(a) in neutral methanol:

234 nm ($E^{1\%}_{1cm} = 206$)

268 nm ($E^{1\%}_{1cm} = 114$)

(b) in methanol containing 0.1 N HCl:

233 nm ($E^{1\%}_{1cm} = 192$)

271 nm ($E^{1\%}_{1cm} = 93$)

(c) in methanol containing 0.1 N NaOH:

251 nm ($E^{1\%}_{1cm} = 275$)

-continued

~300 nm (shoulder)

Figure 3:
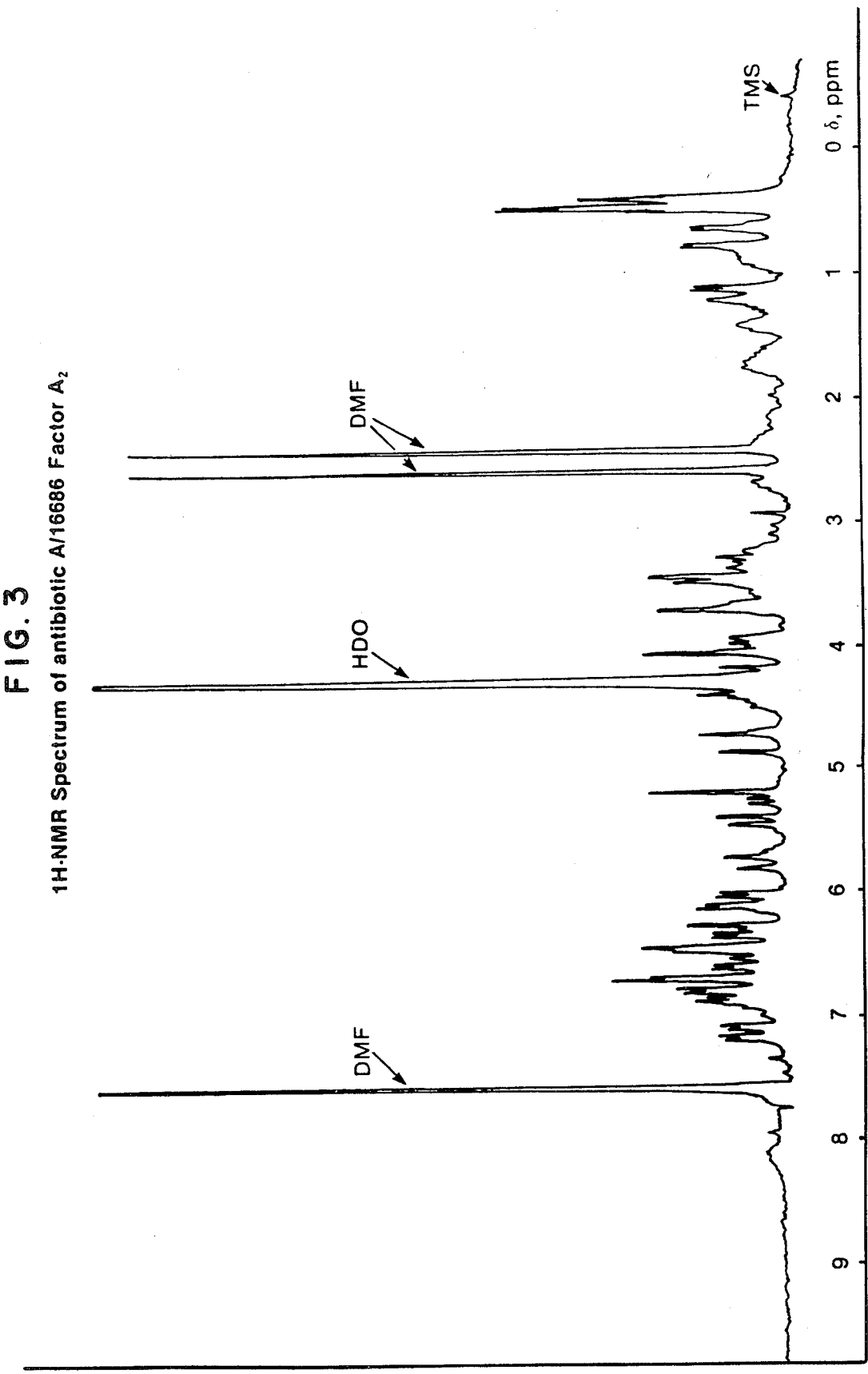

A/16686 factor A$_2$ gives the following signals in 270 MHz H NMR spectrum, FIG. 3, registered in DMF-d$_7$/D$_2$O 1:1 (v/v) solution (TMS as internal standard δ 0.00 ppm) on a Pulse Fourier Transform Bruker WH 270 cryospectrometer:

(i) a group of signals at 0.5–3 ppm corresponding to about 51 aliphatic protons, in particular doublets centred approximately at 1.53 ppm (J=7 Hz) 1.20 ppm (J=6 Hz) and 1.07 ppm (J=5 Hz).

(ii) a group of signals at 3–6.5 ppm corresponding to about 43 protons of olefinic type or protons of carbons linked to hetero atoms, in particular a singlet approximately at 5.62 ppm.

(iii) a group of signals at 6.5–8 ppm corresponding to about 39 protons of aromatic type, in particular doublets centred approximately at 7.60 ppm (J=8 Hz), at 7.49 ppm (J=8 Hz), and at 6.46 ppm (J=8 Hz).

The singlets at 8, 2.85 and 3.01 ppm and the singlet at 4.73 ppm correspond respectively to DMF and HDO present in the solvent mixture.

A/16686 factor A$_2$ has a specific rotation $[\alpha]_D^{20}$, of +73±4° (c=0.49, H$_2$O).

The R$_f$ values of A/16686 factor A$_2$ in various paper-chromatographic systems, using *B. subtilis* ATCC 6633 as a detection organism, are given in the following table:

TABLE IV

Chromatographic behaviour of A/16686 factor A$_2$ (Whatman No. 1 paper)≠

| | Elution system | R$_f$ value |
|---|---|---|
| (1) | n-butanol saturated with Sorensen buffer pH 6.0 | 0.00 |
| (2) | n-butanol saturated with water containing 2% of p-toluenesulfonic acid | 0.00 |
| (3) | n-butanol saturated with water containing 2% of ammonium hydroxide | 0.00 |
| (4) | Sörensen buffer, pH 6.0, saturated with n-butanol | 0.05 |
| (5) | n-butanol:methanol:water: 4:1:2 | 0.48 |
| (6) | ethyl acetate saturated with water | 0.00 |
| (7) | n-butanol:acetic acid:water 2:1:1 | 0.44 |

≠Descending chromatography
Rm: 40 cm
Amounts: 50 μg of the compound dissolved in H$_2$O:CH$_3$CN 1:1 (v/v) (2 mg/ml)

The R$_f$ value of A/16686 factor A$_2$ in various thin-layer chromatographic systems are listed in the following table (the conditions are indicated below the table):

TABLE V

| | Elution system (v/v/v) | R$_f$ value |
|---|---|---|
| (1) | aqueous 2.5% HCOONH$_4$:CH$_3$CN (65:35)* | 0.36 |
| (2) | n-butanol:acetic acid:water 4:2:5 | 0.80 |
| (3) | n-butanol:acetic acid:water 4:2:5 | 0.52 |
| (4) | n-propanol:n-butanol:1N NH$_4$OH 2:3:4 (upper phase) | 0.12 |
| (5) | n-butanol:acetic acid:water 4:1:5 | 0.15 |

Rm: about 140 mm
Amounts: 2 ÷ 5 μl of a solution (1 mg/ml) in CH$_3$CN:H$_2$O 1:1 (v/v)
Visualization: (a) Iodine vapour (b) U.V. light at 254 nm. 1,2-silanised Silicagel 60 F$_{254}$ plates (Merck): visualization a,b;3,4,5 - Silicagel 60 F$_{254}$ plates (Merck): visualization a.
(*Internal standards: Caffeine R$_f$0.60; Cortisone R$_f$0.35; Dexamethasone R$_f$0.30).

A/16686 factor A$_2$ shows the following characteristic reactions:

| | |
|---|---|
| Ninhydrin (3% ethanolic solution) | positive |
| Molish | positive |
| Biuret | positive |
| Millon | negative |
| 1% FeCl$_3$-1% K$_3$Fe(CN)$_6$ aqueous | Green color |
| KMnO$_4$ (acidic) | positive |
| H$_2$SO$_4$ conc. | negative |

Amino acid analysis of A/16686 factor A$_2$ after acid hydrolysis with 6 N hydrochloric acid at 110° C. for 6 hours, revealed the presence of at least the following amino acids: alanine, leucine, glycine, aspartic acid, phenylalanine, ornithine p-hydroxyphenylglycine, and hydroxy, chloro-substituted phenylglycine. Analysis of an acid hydrolyzate of A/16686 factor A$_2$ after 2 hours in 2 N H$_2$SO$_4$ at 100° C., shows the presence of the neutral carbohydrate D-mannose.

HPLC analysis of antibiotic A/16686 factor A$_2$ using a μ-Bondapack ®C$_{18}$, trademark of Waters Company column (3.9 mm ID×300 mm) and a mixture HCOONH$_4$ 0.025 M/CH$_3$CN 60/40 (v/v) as the mobile phase with a flow rate of 2 ml/min, showed that the compound has a retention time (t$_R$) of 4' 99/100" (Internal standards: Anthracene t$_R$ 35' 18/100"; α-Nitronaphthalene t$_R$ 11' 14/100"; Toluene t$_R$ 8' 64/100").

A/16686 Factor A$_1$

A/16686 factor A$_1$ is a white amorphous powder which melts with decomposition at about 210°–220° C. It is very soluble in water, dimethylformamide, and aqueous methanol; is soluble in methanol, and ethanol; but is insoluble in ethyl ether, petroleum ether, and benzene. Elemental analysis of A/16686 factor A$_1$ previously dried at about 140° C. under inert atmosphere, indicates the following approximate percentage composition (average): carbon 50.31% hydrogen, 6.00% nitrogen, 9.92%, residue 6.07%.

Chlorine analysis of A/16686 factor A$_1$ gives the following results: chlorine (total content), 1.61%, chlorine ion, 0.90%.

Figure 4:
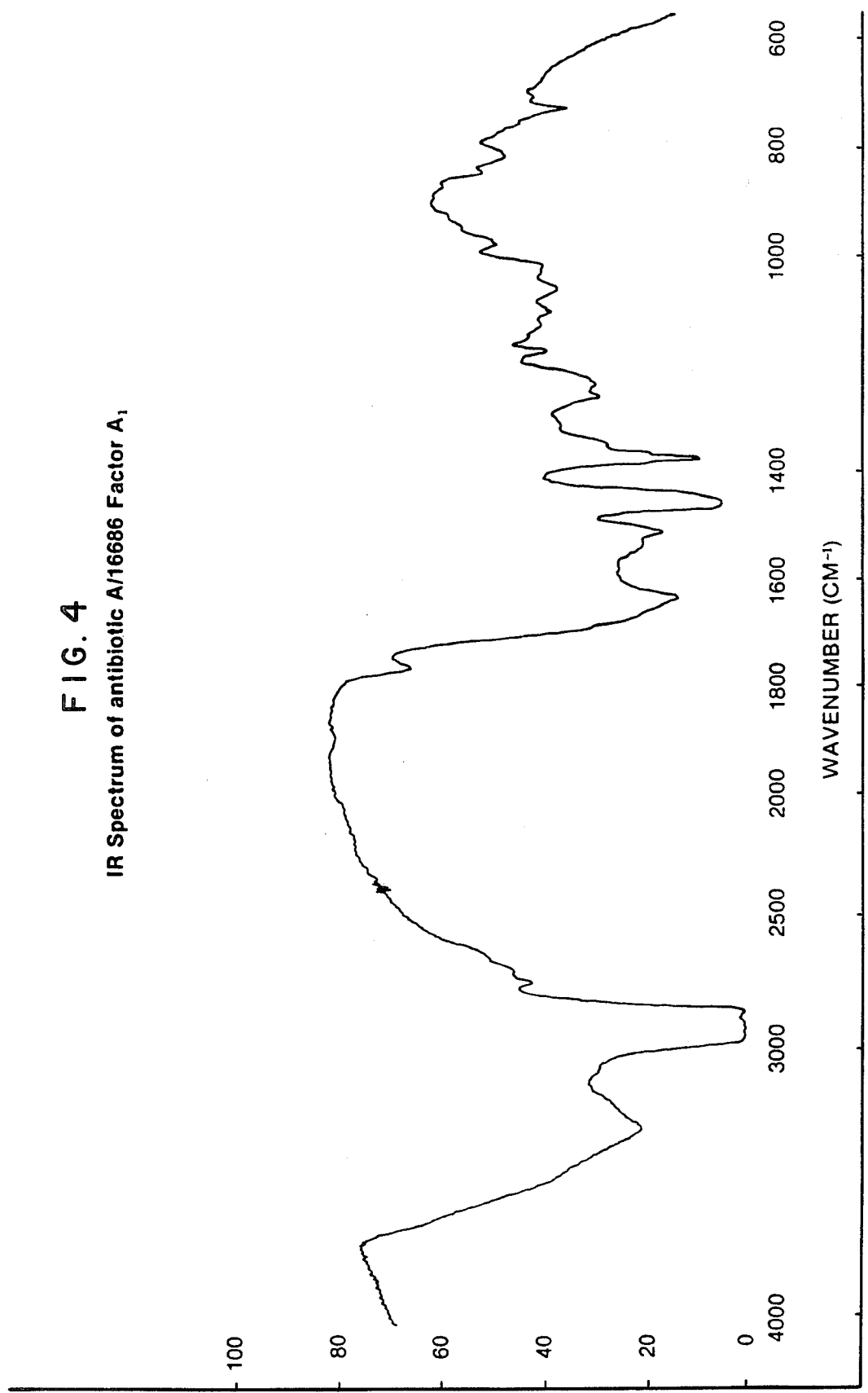

The infrared absorption spectrum of A/16686 factor A$_1$ in nujol is shown in FIG. 4 of the accompanying drawings.

The following absorption maxima are observed: 3290, 2930 and 2860 (nujol), 1765, 1630, 1510, 1455 and 1375 (nujol), 1260, 1235, 1175, 1150, 1130, 1060, 1015, 975, 840, and 810 cm$^{-1}$.

Figure 5:
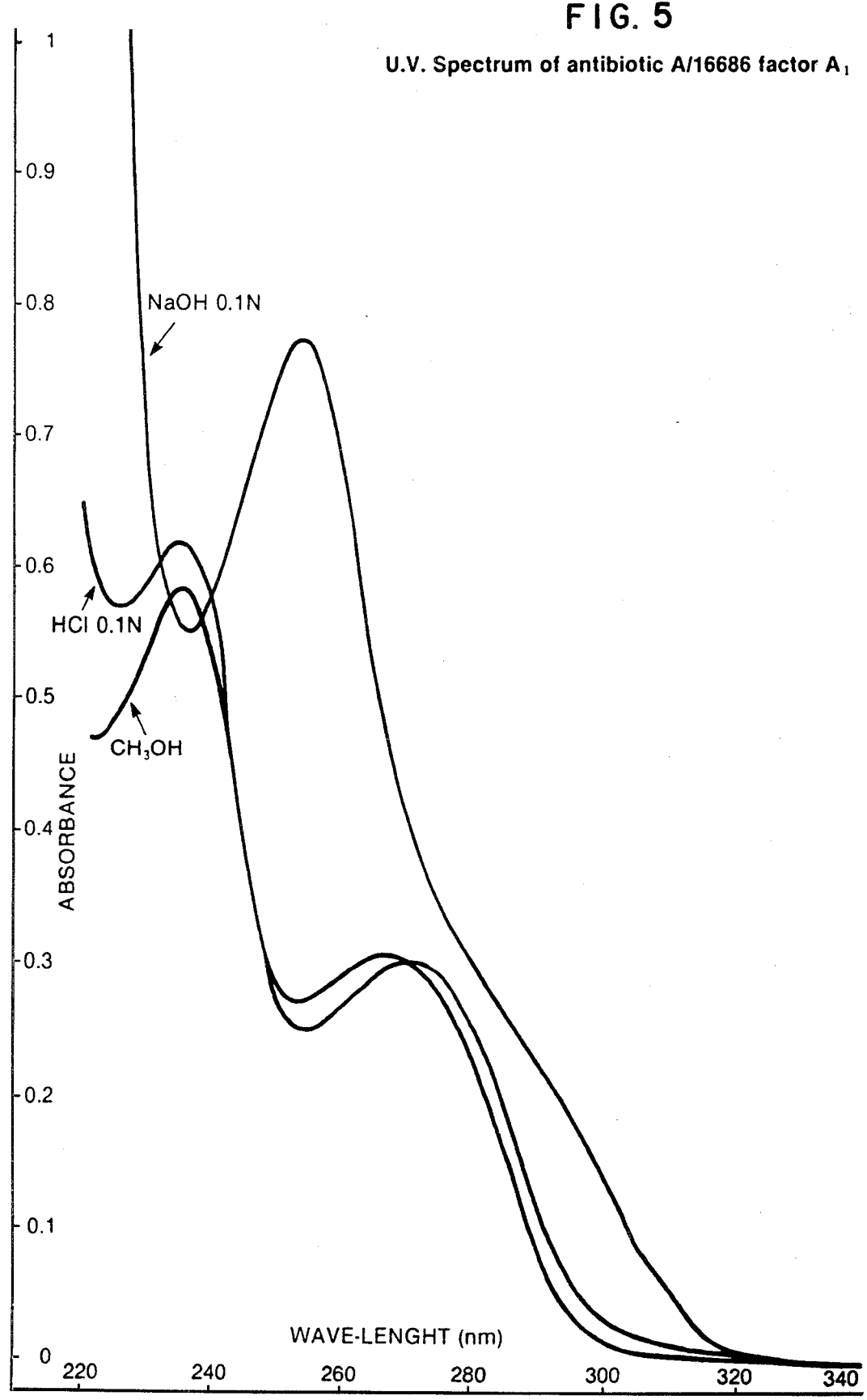

The ultraviolet absorption spectrum of A/16686 factor A$_1$ which is shown in FIG. 5 of the accompanying drawings exhibits the following absorption maxima:

(a) in neutral methanol:

233 nm (E$_{1cm}^{1\%}$ = 202)

266 nm (E$_{1cm}^{1\%}$ = 106)

(b) in methanol containing 0.1 N HCl:

232 nm (E$_{1cm}^{1\%}$ = 219)

270 nm (E$_{1cm}^{1\%}$ = 110)

(c) in methanol containing 0.1 N NaOH:

251 nm (E$_{1cm}^{1\%}$ = 264)

~290 nm (shoulder)

A/16686 factor A$_1$ has a specific rotation, $[\alpha]_D^{20}$, of +57±4° (c=0.51, H$_2$O).

The R$_f$ values of A/16686 factor A$_1$ in various paper-chromatographic systems, using *B. subtilis* ATCC 6633 as a detection organism, are given in the following table.

TABLE VI

Chromatographic behaviour of A/16686 factor A$_1$ (Whatman No. 1 paper)≠

| | Elution system | R$_f$ value |
|---|---|---|
| (1) | n-butanol saturated with Sorensen buffer pH 6.0 | 0.00 |
| (2) | n-butanol saturated with water containing 2% of p-toluene-sulfonic acid | 0.00 |
| (3) | n-butanol saturated with water containing 2% of ammonium hydroxide | 0.00 |
| (4) | Sorensen buffer, pH 6.0, saturated with n-butanol | 0.05 |
| (5) | n-butanol:methanol:water 4:1:2 | 0.48 |
| (6) | ethyl acetate saturated with water | 0.00 |
| (7) | n-butanol:acetic acid:water 2:1:1 | 0.44 |

≠Descending chromatography
Rm: 40 cm
Amounts: 50 μg of the compound dissolved in H$_2$O:CH$_3$CN 1:1 v/v (2 mg/ml)

The R$_f$ values of A/16686 factor A$_1$ in various thin-layer chromatographic systems are listed in the following table (the conditions are indicated below the table):

TABLE VII

| | Elution system (v/v/v) | R$_f$ value |
|---|---|---|
| (1) | Aqueous 2.5% HCOONH$_4$:CH$_3$CN 65:35* | 0.40 |
| (2) | n-butanol:acetic acid:water 4:2:5 | 0.80 |
| (3) | n-butanol:acetic acid:water 4:2:5 | 0.52 |
| (4) | n-propanol:n-butanol:1N NH$_4$OH 2:3:4 (upper phase) | 0.12 |
| (5) | n-butanol:acetic acid:water 4:1:5 | 0.15 |

Rm: about 140 mm
Amounts: 2 ÷ 5 μl of a solution (1 mg/ml) in CH$_3$CN:H$_2$O 1:1 (v/v)
Visualization: (a) Iodine vapour (b) UV-light at 254 nm 1,2-Silanised Silicagel 60 F$_{254}$ plates (Merck): visualization a,b; 3,4,5 - Silicagel 60 F$_{254}$ Merck: visualization a.
(*Internal standards: Caffeine R$_f$ 0.60; Cortisone R$_f$ 0.35; Dexamethasone R$_f$ 0.30).

Amino-acid analysis of A/16686 factor A$_1$, after acidic hydrolisis in 6 N hydrochloric acid at 110° C. for 6 hours, indicates the presence of at least the following amino-acids: alanine, leucine, glycine, aspartic acid, phenylalanine, ornithine, p-hydroxy-phenylglycine, and hydroxy, chloro-substituted phenylglycine.

Analysis of an acid hydrolyzate of A/16686 factor A$_1$ after 2 hours in 2 N H$_2$SO$_4$ at 100° C. shows the presence of the neutral carbohydrate D-mannose.

HPLC analysis of antibiotic A/16686 factor A$_1$ using a μ-Bondapack ®C$_{18}$, trademark of Waters Company, column (3.9 mm ID×300 mm) and a mixture HCOONH$_4$ 0.025 M/CH$_3$CN 60/40 (v/v) as the mobile phase at a flow rate of 2 ml/min gave a t$_R$ of 3' 84/100" (Internal standards: Anthracene t$_R$ 35' 18/100"; α-Nitronaphthalene t$_R$ 11' 14/100"; Toluene 8' 64/100").

A/16686 Factor A$_3$

A/16686 factor A$_3$ is a white amorphous powder which melts with decomposition at about 220° C. It is very soluble in water, dimethylformamide and aqueous methanol; it is soluble in methanol, and ethanol but it is insoluble in ethyl ether, petroleum ether, and benzene.

Figure 6:
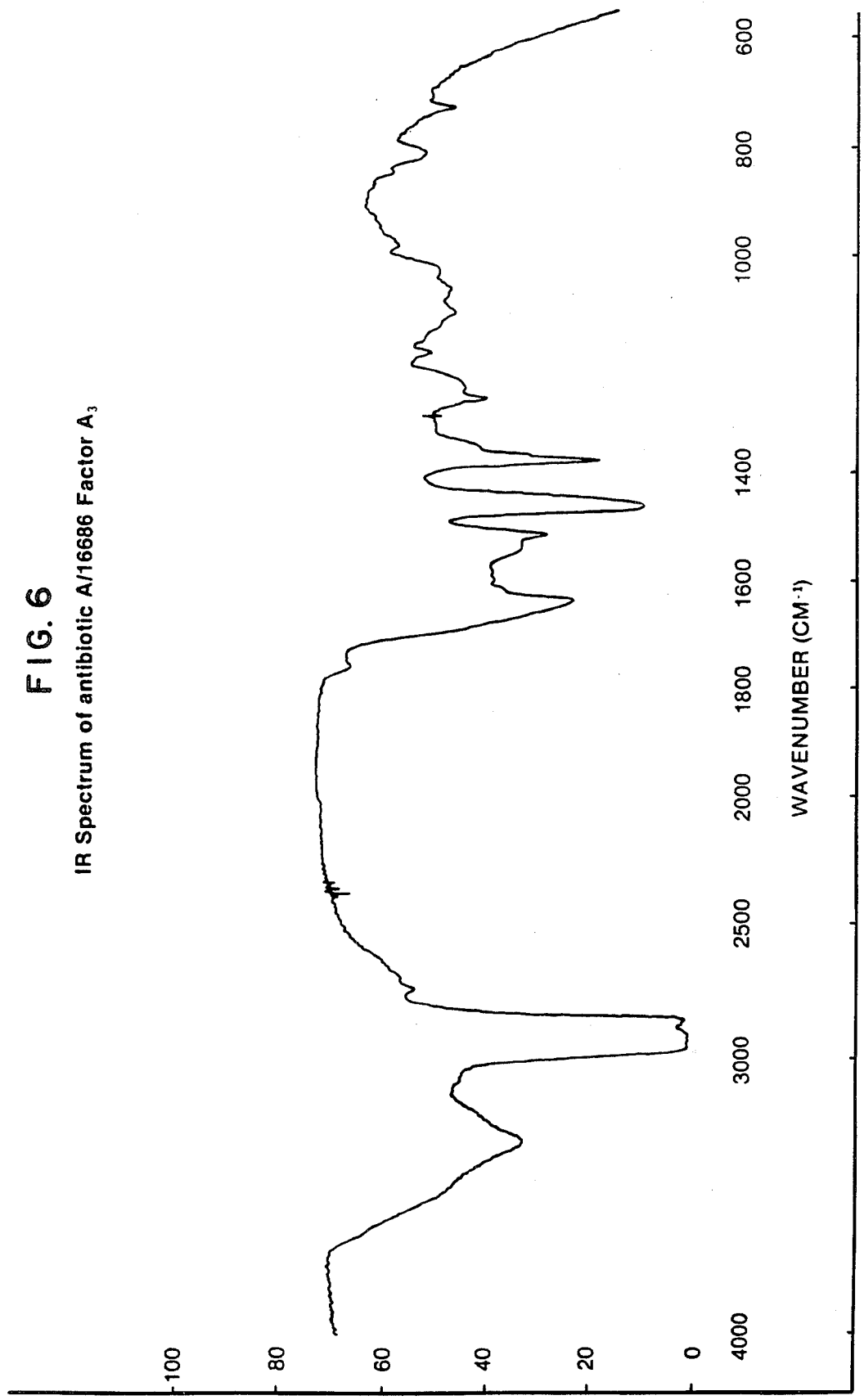

Elemental analysis of A/16686 factor A$_3$ previously dried at about 140° C. under inert atmosphere indicates the following approximate percentage composition (average) carbon, 48.41% hydrogen 5.84%, nitrogen 9.09%; residue 9.1%. Chlorine analysis gives the following results: chlorine (total content), 1.68% chlorine ions, 1.16%. The infrared absorption spectrum of A/16686 factor A$_3$ in nujol is shown in FIG. 6 of the accompanying drawings. The following absorption maxima are observed: 3290, 2930 and 2860 (nujol), 1765, 1635, 1510, 1455 and 1375 (nujol), 1260, 1240, 1175, 1100, 1060, 1020, 975, 840, and 805 cm$^{-1}$.

Figure 7:
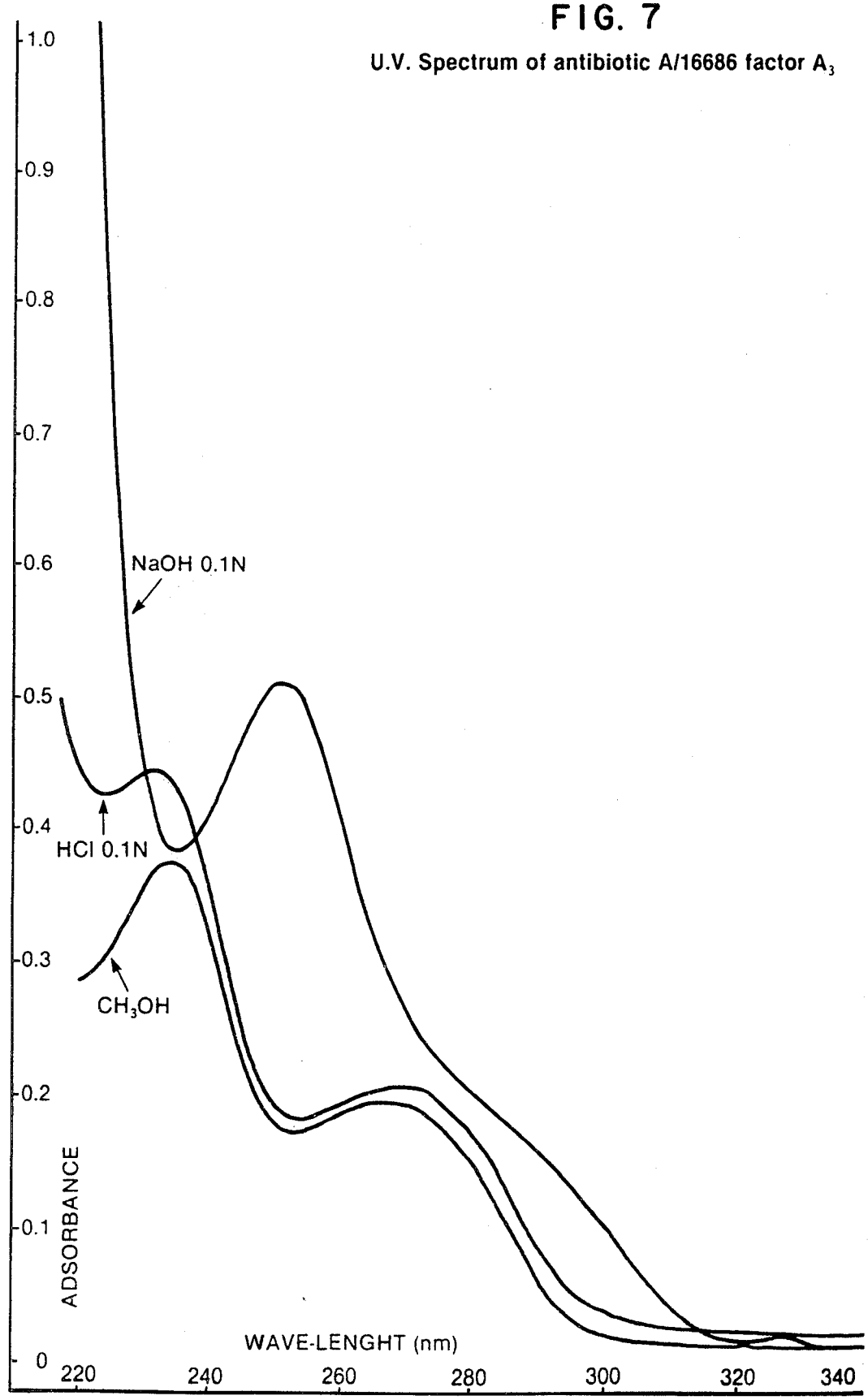

The ultraviolet absorption spectrum of A/16686 factor A$_3$ which is given in FIG. 7 of the accompanying drawings exhibits the following absorption maxima.

(a) in neutral methanol:

$$234 \text{ nm } (E^{1\%}_{1cm} = 147)$$

$$267 \text{ nm } (E^{1\%}_{1cm} = 74)$$

(b) in methanol containing 0.1 N HCl:

$$232 \text{ nm } (E^{1\%}_{1cm} = 132)$$

$$270 \text{ nm } (E^{1}_{1cm} = 76)$$

(c) in methanol containing 0.1 N NaOH:

$$250 \text{ nm } (E^{1\%}_{1cm} = 202)$$

$$\sim 295 \text{ nm (shoulder)}$$

A/16686 factor A$_3$ has a specific rotation, $[\alpha]_D^{20}$, of +50±4° (c=0.48, HCl N/100).

The R$_f$ values of A/16686 factor A$_3$ in various paper-chromatographic systems, using *B. subtilis* ATCC 6633, as a detection organism, are given in the following table:

TABLE VIII

Chromatographic behaviour of A/16686 factor A$_3$ (Whatman No. 1 paper)$^{\neq}$

| | Elution system | R$_f$ value |
|---|---|---|
| (1) | n-butanol saturated with Sorensen buffer pH 6.0 | 0.00 |
| (2) | n-butanol saturated with water containing 2% of p-toluenesulfonic acid | 0.00 |
| (3) | n-butanol saturated with water containing 2% of ammonium hydroxide | 0.00 |
| (4) | Sörensen buffer, pH 6.0 saturated with n-butanol | 0.05 |
| (5) | n-butanol:methanol:water: 4:1:2 | 0.48 |
| (6) | ethyl acetate saturated with water | 0.00 |
| (7) | n-butanol:acetic acid:water 2:1:1 | 0.44 |

$^{\neq}$Descending chromatography
Rm: 40 cm
Amounts: 50 μg of the compound dissolved in H$_2$O:CH$_3$CN 1:1 (v/v) (2 mg/ml)

The R$_f$ value of A/16686 factor A$_3$ in various thin-layer chromatographic systems are listed in the following table (the conditions are indicated below the table):

TABLE IX

| | Elution system | R$_f$ value |
|---|---|---|
| (1) | aqueous 2.5% HCOONH$_4$:CH$_3$CN (65:35)* | 0.32 |
| (2) | n-butanol:acetic acid:water 4:2:5 | 0.80 |
| (3) | n-butanol:acetic acid:water 4:2:5 | 0.52 |
| (4) | n-propanol:n-butanol:1N NH$_4$OH 2:3:4 (upper phase) | 0.12 |

TABLE IX-continued

| | Elution system | R$_f$ value |
|---|---|---|
| (5) | n-butanol:acetic acid:water 4:1:5 | 0.15 |

Rm: about 140 mm
Amounts: 2 ÷ 5 μl of a solution (1 mg/ml) in CH$_3$CN:H$_2$O 1:1
Visualization: (a) Iodine vapour (b) U.V. light at 254 nm. 1,2-silanised Silicagel 60 F$_{254}$ plates (Merck): visualization a, b; 3,4,5 - Silicagel 60 F$_{254}$ plates (Merck): visualization a.
(*Internal standards: Caffeine R$_f$0.60; Cortisone R$_f$0.35; Dexamethasone R$_f$0.30).

Amino-acid analysis A/16686 factor A$_3$ after acid hydrolysis in 6 N hydrochloric acid at 110° C. for 6 hours revealed the presence of at least the following amino-acids: alanine, leucine, glycine, aspartic acid, phenylalanine, ornithine, p-hydroxyphenylglycine, and hydroxy, chloro substituted phenylglycine.

Analysis of an acid hydrolyzate of A/16686 factor A$_3$ after 2 hours in 2 N H$_2$SO$_4$ at 100° C. shows the presence of the neutral carbohydrate D-mannose.

HPLC analysis of antibiotic A/16686 factor A$_3$ using a μ-Bondapack ® C$_{18}$, trademark of Waters Company, column (3.9 mm ID×300 mm) and a mixture HCOONH$_4$ 0.025 M/CH$_3$CN 60/40 (v/v) as the mobile phase at a flow rate of 2 ml/min gave a t$_R$ of 6' 84/100". (Internal standards: Anthracene t$_R$ 35' 18/100"; α-Nitronaphthalene t$_R$ 11' 14/100"; Toluene t$_R$ 8' 64/100").

Antibiotic A/16686 factor A$_2$, as well as factor A$_1$ and A$_3$ are antimicrobial agents and are especially active against gram-positive microorganisms. In particular, the in vitro activity spectrum of the A/16686 antibiotics is summarized in the following Table:

TABLE X

| | MIC (μg/ml) | | |
|---|---|---|---|
| Organisms | Factor A$_1$ | Factor A$_2$ | Factor A$_3$ |
| *S. aureus* ATCC 6538 | 0.1 | 0.1 | 1.6 |
| *S. aureus* Tour (inoculum 10$^3$/ml) | 0.2 | 0.2 | 1.6 |
| *S. aureus* Tour (inoculum 10$^6$/ml) | 0.4 | 0.8 | 3.1 |
| *S. aureus* Tour (+ 30% bovine serum) | 0.4 | 0.8 | 1.6 |
| *S. pyogenes* C 203 SKF 13400 | 0.012 | 0.012 | 0.012 |
| *S. pneumoniae* Felton UC 41 | 0.025 | 0.025 | 0.025 |
| *S. foecium* ATCC 10541 | 0.1 | 0.05 | 0.1 |
| *E. coli* SKF 12140 | >100 | >100 | >100 |

The A/16686 antibiotics have also been found to possess a high order of activity in vivo against various pathogenic organisms. The effectiveness of A/16686 antibiotics is readily apparent from Table XI which gives the ED$_{50}$ values in mice against two different microorganisms.

TABLE XI

| | ED$_{50}$ mg/ml day s.c. | |
|---|---|---|
| | *S. pyogenes* C 203SKF 13400 | *S. pneumoniae* Felton UC 41 |
| A/16686 Factor A$_1$ | 0.041 (0.012–0.064) | 0.15 (0.17–0.14) |
| A/16686 Factor A$_2$ | 0.048 (0.026–0.070) | 0.18 (0.20–0.16) |
| A/16686 Factor A$_3$ | 0.14 (0.096–0.21) | 0.41 (0.46–0.36) |

The A/16686 compounds also inhibit the growth of microorganisms which contribute to the development of periodontal diseases. This important property of the A/16686 compounds was assessed by means of tests using an artificial *Streptococcus mutans* ATCC 25175 plaque system. In these experiments the A/16686 compounds inhibited plaque formation at very low concentration levels. The A/16686 compounds may therefore be employed for the treatment of diseases due to pathogenic organisms susceptible to them. For instance, in the treatment of Streptococcal or Staphylococcal infections or for preventing and treating the dissolution and disintegration of the enamel and dentin of the teeth due to dental caries.

In such treatments the A/16686 compounds may be employed as free bases or as the corresponding nontoxic physiologically acceptable acid addition salts. Moreover they may be employed as single factors or, considering the similarity of their activity pattern, also in the form of mixtures of two or all of the three factors in any proportion.

In order to illustrate more fully the operation of this invention, the following examples are provided.

EXAMPLE 1

Fermentation of the strain Actinoplanes sp. ATCC 33076

A culture of Actinoplanes sp. ATCC 33076 is precultured by growing the strain in shake-flasks containing 100 ml each of an aqueous nutrient medium having the following composition (in g/l):

| meat extract | 3 g/l |
| yeast extract | 5 g/l |
| tryptone | 5 g/l |
| soluble starch | 24 g/l |
| glucose | 1 g/l |
| CaCO$_3$ | 4 g/l |

The flasks are shaken for about 96 hours at 28°–20° C. and then are poured into a jar fermentor containing 4 of the same vegetative medium and precultured for 48 hours at the same temperature. 3 l of this preculture are then used to inoculate a larger jar fermentor containing 30 l of the same nutrient medium seen above and aerobically precultured for 24 hours at 28° C. Finally, 20 l of this preculture are used to inoculate a tank fermentor containing 200 ml of an aqueous nutrient medium having the following composition:

| meat extract | 4 g/l |
| peptone | 4 g/l |
| yeast extract | 1 g/l |
| sodium chloride | 2.5 g/l |
| soybean meal | 10 g/l |
| glucose | 25 g/l |
| CaCO$_3$ | 5 g/l |

The fermentation batch is incubated aerobically under stirring at 28°–30° C. At intervals, the antibiotic activity is assayed microbiologically by the agar diffusion method using *Sarcina lutea* ATCC 9341 as the test organism. The maximum activity is reached after 72 to 120 hours of fermentation.

EXAMPLE 2

Separation of the antibiotic A/16686 complex

Whole fermentation broth (170 l) prepared as described in Example 1 is cooled to 10° C. and brought to pH 3.5 by means of 18% HCl. The resulting acidic broth is filtered using a filter aid (Clarcel Flow-Ma), and the mycelial cake is washed with water.

Methanol (30 l) is used to extract the mycelial mass which, after filtration, is extracted again with a mixture methanol/water (30 l of methanol plus 5 l of water).

The exhausted mycelium is discarded and the two methanol extracts are concentrated under vacuum at a temperature lower than 40° C. to yield an aqueous concentrate (6 l). This aqueous concentrate is extracted with three portions, 10 l each, of n-butanol, which are combined and concentrated to a small volume under vacuum.

This concentrate is added to petroleum ether and the resulting precipitate is separated by decantation and added to a further amount of petroleum ether. The precipitate is separated by filtration and dried under vacuum at room temperature to give 80 g of antibiotic A/16686 complex as a raw material having a M.I.C. against *S. pneumoniae* UC 41 of 0.1 µg/ml.

EXAMPLE 3

Purification of the antibiotic A/16686 complex (a) 47.7 g of the raw antibiotic A/16686 complex obtained in Example 2 are treated with 1.4 l of a chloroform:ethanol:water mixture (4:7:2) (v/v/v) and the oily product which forms is separated from the solution by decantion. Further 70 ml of the above mixture are then added to the oily product and the separation is repeated. By treatment of the oily product with water (440 ml), it solidifies and is separated by centrifugation or filtration:

The solid, which is separated, is suspended in water (170 ml), dissolved by addition of methanol (400 ml) and filtered. The pH of the aqueous methanol solution is brought to 3.5 by the addition of 1 N HCl, then the solvents are stripped under vacuum by adding n-butanol at a temperature never higher than 35° C., to give a butanol concentrate of about 50 ml. By addition of diethyl ether (500 ml) a precipitate forms which is separated by filtration and dried under vacuum at room temperature yielding 1.012 g of rather pure antibiotic A/16686 complex having a M.I.C. on *S. pyogenes* of 0.025 µg/ml.

(b) 1.58 g of antibiotic A/16686 complex obtained as described before are dissolved in 100 ml of a mixture acetonitrile:H$_2$O 1:1 (v/v) and the resulting solution is applied to a column containing 430 g of Silicagel 60 (Merck 0.06–0.2 mm) prepared in the same mixture. The column is developed first using the same acetonitrile-water mixture and collecting 70 fractions of 20 ml each, and then using acetonitrile:N/100 HCl 1:1 (v/v) and collecting further 290 fractions, of 20 ml each.

Elution of the column is monitored by thin layer chromatography on 60 F$_{254}$ Silicagel plates and by assaying fractions against *Sarcina lutea*.

Fractions 130 to 265 are combined and the solvents are stripped under vacuum with n-butanol to give a n-butanol concentrate of 20 ml. This residual volume is poured into a large amount of ethyl ether and the precipitate which form is separated by filtration and dried under vacuum at room temperature over P$_2$O$_5$ yielding 1.015 g of antibiotic A/16686 complex.

(c) 0.67 g of the above substance are dissolved in 24 ml of water and 76 ml of methanol. The resulting solution is applied to a 3.0×62.0 cm column containing 220 g of Sephadex LH-20, prepared in methanol:water 7:3 (v/v). The column is developed with the same mixture collecting 10 ml fractions. Fractions containing antibiotic A/16686 complex are combined and the solvents are stripped under vacuum at a temperature lower than 35° C. with n-butanol to a residual butanol volume of about 10 ml. This solution is added to ethyl ether to precipitate pure antibiotic A/16686 complex. The precipitate is separated by filtration washed with ethyl ether and dried under vacuum over $P_2O_5$ at room temperature yielding 0.26 g of pure antibiotic A/16686 complex.

The antibiotic A/16686 complex thus obtained is a white, crystalline material slightly hygroscopic which melts at 224°–226° C. It is very soluble in water and dimethylformamide, soluble in methanol, ethanol, propanol and butanol, but is insoluble in ethyl ether, petroleum ether and benzene. Elemental analysis of the antibiotic A/16686 complex thus obtained, previously dried at 140° C. under inert atmosphere, indicates the following approximate percentage composition (as an average of several analyses): carbon 51.73%; hydrogen 6.34%; nitrogen 9.96%; residue 1%. Chlorine analysis gives the following results: chlorine (total content) 5.48%; chlorine ions 4.74%. The infrared absorption spectrum in nujol exhibits the following absorption maxima (in $cm^{-1}$): 3290, 3070, 2930 and 2860 (nujol), 1765, 1630, 1510, 1455 e 1375 (nujol), 1230, 1175, 1130, 1065, 1030, 1015, 980, 840 and 820.

The ultraviolet absorption spectrum of the antibiotic A/16686 complex obtained as described in example 3 exhibits the following absorption maxima:

(a) in methanol:

$$232 \text{ nm } (E^{1\%}_{1cm} = 178)$$

$$265 \text{ nm } (E^{1\%}_{1cm} = 107)$$

(b) in methanol containing 0.1 N HCl:

$$231 \text{ nm } (E^{1\%}_{1cm} = 167)$$

$$270 \text{ nm } (E^{1\%}_{1cm} = 96)$$

(c) in methanol containing 0.1 N NaOH:

$$250 \text{ nm } (E^{1\%}_{1cm} = 232)$$

$$295 \text{ nm (shoulder)}$$

(d) in methanol containing pH 7.38 buffer:

$$231 \text{ nm } (E^{1\%}_{1cm} = 167)$$

$$270 \text{ nm } (E^{1\%}_{1cm} = 96)$$

It has a specific rotation, $[\alpha]_D^{24}$, of +49.7° (c=0.43% in DMF).

The $R_f$ values of antibiotic A/16686 complex in various paper-chromatographic systems, using *S. aureus* ATCC 6538 as a detection organism, are given in the following table:

TABLE XII

Chromatographic behaviour (Whatman No. 1 paper)≠ of antibiotic A/16686 complex

| | Elution system | $R_f$ value |
|---|---|---|
| (1) | n-butanol saturated with Sorensen buffer pH 6.0 | 0.00 |
| (2) | n-butanol saturated with water containing 2% of p-toluenesulfonic acid | 0.00 |
| (3) | n-butanol saturated with water containing 2% ammonium hydroxide | 0.00 |
| (4) | Sörensen buffer, pH 6.0, saturated with n-butanol | 0.05 |
| (5) | n-butanol:methanol:water 4:1:2 | 0.43 |
| (6) | ethyl acetate saturated with water | 0.00 |
| (7) | n-butanol:acetic acid:water 2:1:1 | 0.52 |

TABLE XII-continued

Chromatographic behaviour (Whatman No. 1 paper)≠ of antibiotic A/16686 complex

| | Elution system | $R_f$ value |
|---|---|---|
| (8) | n-butanol:pyridine:water 4:3:7 | 0.87 |

≠Descending chromatography
Rm: 40 cm
Amounts: 20 μg of the compound dissolved in water methanol (2 mg/ml)

The $R_f$ values of antibiotic A/16686 complex in various thin-layer chromatographic systems are listed in the following table (the conditions are indicated below the table):

TABLE XIII

| | Elution systems (v/v/v) | $R_f$ values |
|---|---|---|
| (1) | n-propanol:n-butanol:N ammonium hydroxide 2:3:4 (upper phase) | 0.15 |
| (2) | n-butanol:acetic acid:water 4:2:5 | 0.61 |
| (3) | n-butanol:ethanol:0.1 N hydrochloric acid | 0.61 |
| (4) | chloroform:ethanol:10% acetic acid 4:7:2 | 0.00 |
| (5) | n-butanol:acetic acid:water 4:1:5 | 0.17 |
| (6) | methanol:10% aqueous ammonium acetate:10% ammonium hydroxide 10:9:1 | 0.52 |
| (7) | n-butanol:pyridine:water:acetic acid 6:4:3:1 | 0.45 |
| (8) | methanol:10% aqueous ammonium acetate:10% ammonium hydroxide 10:9:1 | 0.11 |
| (9) | 0.25 M aqueous $NaH_2PO_4$:acetonitrile 1:1 | 0.68 |
| (10) | methanol:10% aqueous ammonium acetate 1:1 | 0.65 |
| (11) | n-butanol:acetic acid:water 4:2:5 | 0.77 |

Rm: about 140 mm
Amounts: 2 ÷ 5 μl of a solution (1 mg/ml) of the compound in acetonitrile-water 1:1 (v/v)
Visualization: (a) bioautography on agar plates seeded with *B. subtilis* ATCC 6633; (b) carbonisation by heating with α-naphtholsulfuric acid; (c) Iodine vapour; (d) chlorine-toluidine reagent; (e) UV-light at 254 nm
1 to 7-Silicagel 60 $F_{254}$ plates (Merck); Visualization a, b, c, d, e
8,9-Silicagel 60 $F_{254}$ silanised (Merck); Visualization e
10,11-Cellulose F plates (Merck); Visualization a, e.

HPLC analysis of antibiotic A/16686 complex, isolated and purified as described in example 3, revealed the presence of three factors named antibiotic A/16686 factor $A_1$, $A_2$, and $A_3$ of which the major factor, amounting to approximately 70–87%, is A/16686 factor $A_2$. More particularly, the results of the HPLC analysis and the conditions in which it was performed are illustrated in the following table (Toluene, α-nitronaphthalene and anthracene have been used as internal standards):

TABLE XIV

| Peak No. | $t_R$ |
|---|---|
| $A_1$ | 3' 84/100" |
| $A_2$ | 4' 99/100" |
| $A_3$ | 6' 84/100" |
| Toluene | 8' 64/100" |
| α-Nitronaphthalene | 11' 14/100" |
| Anthracene | 35' 18/100" |

Column: μ Bondapack ® $C_{18}$ (3.9 mm ID × 300 mm)
Mobile phase: $HCOONH_4$ 0.025 M:$CH_3CN$ 60:40 (v/v)
Flow: 2 ml/min
Pressure: 2000 psi
Detector: UV 254 nm

EXAMPLE 4

Separation of antibiotic A/16686 factors $A_1$, $A_2$, and $A_3$

A/16686 complex (169 mg) obtained as described in example 3 is dissolved in 0.01 N hydrochloric acid (6.5 ml) and distilled water (10.4 ml). By reverse phase HPLC [column: μ-Bondapack ®$C_{18}$, trademark of Waters Company, (7.8 mm ID×300 mm)—flow: 4 ml/min—pressure: 2000 psi—mobile phase: $HCOONH_4$ 0.025 M: $CH_3CN$ 65:35 (v/v)] with repeated injections of 1 or 2 ml of the above solution, fractions containing the single factors are collected and further checked by means of analytical HPLC. The fractions are concentrated under vacuum at a temperature lower than 35° C. by adding butanol in order to reduce foam formation. The residual solutions are lyophilized and the obtained solids are separately taken up with distilled water and lyophilized again yielding antibiotic A/16686 factors $A_1$ (10 mg), $A_2$ (95 mg), and $A_3$ (12 mg). By lyophilizing a hydrochloric solution of A/16686 factor $A_2$ obtained as above, the corresponding hydrochloride is obtained as an amorphous white powder which decomposes at 250° C.

EXAMPLE 5

Separation of antibiotic A/16686 factor $A_2$

Antibiotic A/16686 complex (100 mg), obtained as described in example (3b) (titre: ~40%) is dissolved in 0.1 N hydrochloric acid (15 ml). The resulting solution is applied to a column of Amberlite ®XAD-2, trademark of Rohm and Haas Co., (136 ml, height of the bed: 60 cm), previously washed with $CH_3CN$ and with distilled water. The column is developed with a linear gradient 0 to 34% $CH_3CN$/water (v/v) elution, collecting 250 10-ml fractions.

Fractions 185 to 225 which contain A/16686 factor $A_2$ alone, are combined and concentrated under vacuum at a temperature lower than 35° C. by adding butanol in order to reduce foam formation. The residual solution is lyophilized yielding antibiotic A/16686 factor $A_2$ (6.7 mg).

EXAMPLE 6

Separation of antibiotic A/16686 factor $A_2$

Antibiotic A/16686 complex (100 mg) obtained as described in example (3a) (titre: 53.5%) is dissolved in 10 ml of $CH_3CN$/0.025 M aqueous $HCOONH_4$ 27/73 (v/v). The resulting solution is applied to a column of Amberlite ®XAD-2 (200 ml—height of the bed: 52 cm), previously washed with 0.025 M $HCOONH_4$ first and then with $CH_3CN$/0.025 M $HCOONH_4$ 27/73 (v/v). The column is developed with a linear gradient 27 to 40% $CH_3CN$/0.025 M $HCOONH_4$ collecting 10 ml fractions up to 400 ml and then 6 ml fractions up to a total volume of eluent of 2 liters. The eluted fractions are checked by analytical HPLC, combined according to factor content and titrated by HPLC, giving the following results:

| Fractions | % A/16686 factor $A_1$ | % A/16686 factor $A_2$ | % A/16686 factor $A_3$ |
| --- | --- | --- | --- |
| 31–41 | 90.1 | 9.9 | 0 |
| 42–50 | 53.9 | 46.1 | 0 |
| 51–59 | 17.9 | 82.1 | 0 |
| 60–65 | 4.4 | 93.7 | 1.9 |
| 66–75 | 0 | 94.2 | 5.8 |
| 76–80 | 0 | 83.7 | 16.3 |
| 81–99 | 0 | 46.1 | 53.8 |
| 100–110 | 0 | 6.7 | 93.3 |

Fractions 60 to 75 which contain 94% pure Antibiotic A/16686 factor $A_2$ are concentrated under vacuum at a temperature lower than 35° C. by adding butanol and the residual solution is lyophilized, taken up with distilled water and lyophilized again yielding 19.7 mg of A/16686 factor $A_2$.

EXAMPLE 7

Separation of antibiotic A/16686 factor $A_1$ and $A_2$

A solution of antibiotic A/16686 complex (650 mg) obtained as described in Example (3a) (titre 53.5%) is dissolved in a mixture $CH_3CN$/$HCOONH_4$ 0.025 M 26/74 (v/v) and the obtained solution is percolated through a column of Amberlite XAD-2 ®, trademark of Rohm and Haas Co., (1900 ml-height of the bed: 130 cm) previously washed with the same solvent mixture, at a flow of ~9 ml/min.

A 100-ml volume is collected, then the column is developed with the same solvent system at the same flow collecting 300 ml fractions up to 18.3 l and then 500 ml fractions up to a total volume of 21.3 l. The eluted fractions are checked by analytical HPLC, combined according to factor content and titrated by HPLC giving the following results:

| | % A/16686 Factor $A_1$[≠] | % A/16686 Factor $A_2$[≠] | % A/16686 Factor $A_3$[≠] | A/16686 Factor $A_1$[≠≠](mg) | A/16686 Factor $A_2$[≠≠](mg) | A/16686 Factor $A_3$[≠≠](mg) | Total (mg) |
| --- | --- | --- | --- | --- | --- | --- | --- |
| A/16686 complex as obtained in Ex. 3a | 17.4 | 71.0 | 11.6 | 60.5 | 246.4 | 40.3 | 347 |
| Fractions | | | | | | | |
| 19 ÷ 24 | 100 | 0 | 0 | 14.4 | — | — | 14.4 |
| 25 — 26 | 80 | 20 | 0 | 8.2 | 2.1 | — | 10.3 |
| 27 | 73.8 | 26.2 | 0 | 3.6 | 1.3 | — | 4.9 |
| 28 ÷ 31 | 42.2 | 57.8 | 0 | 9.5 | 13.1 | — | 22.6 |
| 32 ÷ 35 | 15 | 85 | 0 | 4.8 | 27.2 | — | 32 |
| 36 ÷ 38 | 3.4 | 96.6 | 0 | 1.2 | 33.6 | — | 34.8 |
| 39 ÷ 48 | 0 | 100 | 0 | — | 107.1 | — | 107.1 |
| 49 ÷ 58 | 0 | 92.7 | 7.3 | — | 40.8 | 3.2 | 44.0 |
| 59 ÷ 61 | 0 | 70.8 | 29.2 | — | 4.0 | 1.7 | 5.7 |
| 62 — 63 | 0 | 43.5 | 56.5 | — | 2.6 | 3.4 | 6.0 |
| 64 ÷ 67 | 0 | 10.6 | 89.4 | — | 3.3 | 28 | 31.3 |

[≠]calculated on the basis of the relative peaks' height
[≠≠]determined by comparing the height of the relative peak with that of a standard sample of A/16686 factor $A_2$

We claim:

1. Antibiotic A/16686 factor $A_2$ as an essentially pure individual antibiotic compound, and its non-toxic physiologically-acceptable acid addition salts, characterized in the form of free base, by:
    (A) being a white amorphous powder which melts with decomposition at 210°–220° C.

(B) being very soluble in water, dimethylformamide, aqueous methanol, and 0.1 N HCl; sparingly soluble in absolute ethanol and butanol; and precipitating from the aqueous solution by the addition of a precipating amount of a solution saturated with NaHCO₃;

(C) an elemental analysis showing 54.57 percent carbon, 6.19 percent hydrogen, 10.88 percent nitrogen, and 1.37 percent chlorine;

(D) an infrared absorption spectrum in nujol with the following observable absorption maxima: 3290, 2930, and 2860 (nujol), 1765, 1635, 1510, 1455 and 1375 (nujol), 1240, 1175, 1130, 1060, 1015, 975, 840 and 815 $cm^{-1}$;

(E) an ultraviolet absorption spectrum with the following absorption maxima:

(a) in neutral methanol:

234 $nm$ ($E_{1cm}^{1\%} = 206$)

268 $nm$ ($E_{1cm}^{1\%} = 114$)

(b) in methanol containing 0.1 N HCl:

233 $nm$ ($E_{1cm}^{1\%} = 192$)

271 $nm$ ($E_{1cm}^{1\%} = 93$)

(c) in methanol containing 0.1 N NaOH:

251 $nm$ ($E_{1cm}^{1\%} = 275$)

300 $nm$ (Shoulder)

(F) a specific rotation $[\alpha]_D^{20}$, of +73±4° (c=0.49, H₂O)

(G) the following $R_f$ values in paper chromatography on Whatman No. 1 paper, using *B. Subtilis* ATCC 6633 as a detection organism:

| Elution system (v:v:v) | $R_f$ value |
|---|---|
| (1) n-butanol saturated with Sörensen buffer pH 6.0 | 0.00 |
| (2) n-butanol saturated with water containing 2% of p-toluenesulfonic acid | 0.00 |
| (3) n-butanol saturated with water containing 2% of ammonium hydroxide | 0.00 |
| (4) Sörensen buffer, pH 6.0, saturated with n-butanol | 0.05 |
| (5) n-butanol:methanol:water 4:1:2 | 0.48 |
| (6) ethyl acetate saturated with water | 0.00 |
| (7) n-butanol:acetic acid:water 2:1:1 | 0.44 |

(H) the following $R_f$ values in the Silicagel thin-layer chromatographic systems indicated below:

| Elution system (v:v:v) | $R_f$ value |
|---|---|
| (1) aqueous 2.5% HCOONH₄:CH₃CN 65:35* | 0.36 |
| (2) n-butanol:acetic acid:water 4:2:5 | 0.80 |
| (3) n-butanol:acetic acid:water 4:2:5 | 0.52 |
| (4) n-propanol:n-butanol:1N NH₄OH | 0.12 |
| (5) n-butanol:acetic acid:water 4:1:5 *2:3:4 (upper phase)* | 0.15 |

1,2 - on silanised Silicagel 60F₂₅₄ plates
3,4,5 - on Silicagel 60F₂₅₄ plates
*Internal standards: Caffeine $R_f$0.60; Cortisone $R_f$0.35; Dexamethasone $R_f$0.30)

(I) an amino-acid analysis, after acidic hydrolysis in 6 N hydrochloric acid at 110° C. for 6 hours, which indicates the presence of at least the following amino-acids: alanine, leucine, glycine, aspartic acid, phenylalanine, ornithine, p-hydroxyphenylglycine, and hydroxy, chloro-substituted phenylglycine;

(J) a carbohydrate analysis of the acid hydrolyzate after 2 hours in 2 N H₂SO₄ at 100° C. which indicates the presence of D-mannose;

(K) the following characteristic reactions:

| | |
|---|---|
| Ninhydrin (3% ethanolic solution) | positive |
| Molish | positive |
| Biuret | positive |
| Millon | negative |
| 1% FeCl₃-1% K₃Fe(CN)₆ aqueous | Green color |
| KMnO₄ (acidic) | positive |
| H₂SO₄ conc. | negative | and (L) a retention time ($t_R$) of 4' 99/100" when analyzed by reverse phase HPLC using an octadecylsilanized silica gel column (3.9 mm ID×300 mm) and a mixture HCOONH₄ 0.025 M/CH₃CN 60/40 (v/v) as the mobile phase with a flow rate of 2 ml/min (Internal standards: Anthracene $t_R$ 35' 18/100"; α-Nitronaphthalene $t_R$ 11' 14/100"; Toluene $t_R$ 8' 64/100"), and, in the form of its hydrochloride, by (M) a melting point of 250° C. (with decomposition).

2. A process for producing antibiotic A/16686 factor A₂ as defined in claim 1, which comprises culturing the strain Actinoplanes sp. ATCC 33076 under submerged aerobic fermentation conditions, in an aqueous nutrient medium containing assimilable sources of carbon and nitrogen, and inorganic salts, recovering said antibiotic activity consisting of antibiotic A/16686 factor A₂ in the form of a complex with other two minor factors named antibiotic A/16686 factors A₁ and A₃ from the fermentation medium, by extraction of the mycelial mass with an organic solvent selected from the group consisting of lower alkanols and acetone, separating antibiotic A/16686 factor A₂ from the antibiotic complex and isolating it as an essentially pure individual antibiotic compound.

3. A process as in claim 2 wherein the extracting solvent is methanol.

4. A process as defined in claim 2 wherein antibiotic A/16686 factor A₂ is separated by column chromatography using a polystyrene resin column and mixtures of water and acetonitrile or mixtures of aqueous ammonium formiate and acetonitrile as the eluting system.

5. A process as defined in claim 2 further characterized in that the three factors A₁, A₂, and A₃ are separately isolated.

6. A process as in claim 2 or 5 wherein separation is achieved by reverse phase HPLC using an octadecylsilanized silica gel column and mixtures of aqueous ammonium formiate and acetonitrile in variable ratios as the mobile phase.

7. An antibiotic substance selected from the group consisting of antibiotic A/16686 factor $A_1$ free base, and its non-toxic, physiologically-acceptable acid addition salts, characterized by:

(A) being a white amorphous material which melts with decomposition at 210°–220° C.;

(B) being very soluble in water, dimethylformamide, and aqueous methanol; soluble in methanol and ethanol; but insoluble in ethyl ether, petroleum ether and benzene;

(C) an elemental analysis showing 50.31 percent carbon, 6.00 percent hydrogen, 9.92 percent nitrogen, 1.61 percent chlorine (total content), 0.90 percent chlorine ions, residue 6.07%;

(D) an infrared absorption spectrum in nujol with the following observable absorption maxima: 3290, 2930 and 2860 (nujol), 1765, 1630, 1510, 1455 and 1375 (nujol), 1260, 1235, 1175, 1150, 1130, 1060, 1015, 975, 840, and 810 cm$^{-1}$;

(E) an ultraviolet absorption spectrum with the following absorption maxima:
  (a) in neutral methanol:

233 nm ($E^{1\%}_{1cm}$ = 202)

266 nm ($E^{1\%}_{1cm}$ = 106)

(b) in methanol containing 0.1 N HCl:

232 nm ($E^{1\%}_{1cm}$ = 219)

270 nm ($E^{1\%}_{1cm}$ = 110)

(c) in methanol containing 0.1 N NaOH:

251 nm ($E^{1\%}_{1cm}$ = 264)

~290 nm (shoulder)

(F) a specific rotation, $[\alpha]_D^{20}$, of $+57\pm4°$ (c=0.51, H$_2$O);

(G) the following $R_f$ values in paper chromatography on Whatman No. 1 paper, using B. subtilis ATCC 6633 as a detection system:

| Elution system (v:v:v) | $R_f$ value |
| --- | --- |
| (1) n-butanol saturated with Sörensen buffer pH 6.0 | 0.00 |
| (2) n-butanol saturated with water containing 2% of p-toluenesulfonic acid | 0.00 |
| (3) n-butanol saturated with water containing 2% of ammonium hydroxide | 0.00 |
| (4) Sörensen buffer, pH 6.0, saturated with n-butanol | 0.05 |
| (5) n-butanol:methanol:water 4:1:2 | 0.48 |
| (6) ethyl acetate saturated with water | 0.00 |
| (7) n-butanol:acetic acid:water 2:1:1 | 0.44 |

(H) the following $R_f$ values in the Silicagel thin-layer chromatographic systems indicated below

| Elution system (v:v:v) | $R_f$ value |
| --- | --- |
| (1) aqueous 2.5% HCOONH$_4$:CH$_3$CN 65:35* | 0.40 |
| (2) n-butanol:acetic acid:water 4:2:5 | 0.80 |
| (3) n-butanol:acetic acid:water 4:2:5 | 0.52 |
| (4) n-propanol:n-butanol:1N NH$_4$OH 2:3:4 (upper phase) | 0.12 |
| (5) n-butanol:acetic acid:water 4:1:5 | 0.15 |

1,2-on silanised Silicagel 60 F$_{254}$ plates
3,4,5-on Silicagel 60 F$_{254}$ plates
*(Internal standards: Caffeine $R_f$ 0.60; Cortisone $R_f$ 0.35; Dexamethasone $R_f$ 0.30);

(I) an amino-acid analysis, after acidic hydrolysis in 6 N hydrochloric acid at 110° C. for 6 hours, which indicates the presence of at least the following amino-acids: alanine, leucine, glycine, aspartic acid, phenylalanine, ornithine, p-hydroxy-phenylglycine, and hydroxy, chloro-substituted phenylglycine;

(J) a carbohydrate analysis of the acid hydrolyzate after 2 hours in 2 N H$_2$SO$_4$ at 100° C. which indicates the presence of D-mannose;

(K) a retention time ($t_R$) of 3' 84/100" when analyzed by reverse phase HPLC using an octadecylsilanized silica gel column (3.9 mm ID×300 mm), and a mixture HCOONH$_4$ 0.025 M/CH$_3$CN 60/40 (v/v) as the mobile phase with a flow rate of 2 ml/min (Internal standards: Anthracene $t_R$ 35' 18/100"; α-Nitronaphthalene $t_R$ 11' 14/100"; Toluene $t_R$ 8' 64/100").

8. An antibiotic substance selected from the group consisting of antibiotic A/16686 factor $A_3$ free base, and its non-toxic physiologically-acceptable acid addition salts, characterized, by:

(A) being a white amorphous powder which melts with decomposition at 220° C.;

(B) being very soluble in water, dimethylformamide and aqueous methanol; soluble in methanol and ethanol; but insoluble in ethyl ether; petroleum ether; and benzene;

(C) an elemental analysis showing 48.41 percent carbon, 5.84 percent hydrogen, 9.09 percent nitrogen, 1.68 percent chlorine (total content), 1.16 percent chlorine ions; residue 9.1%;

(D) an infrared absorption spectrum in nujol with the following observable absorption maxima: 3290, 2930 and 2860 (nujol), 1765, 1635, 1510, 1455 and 1375 (nujol), 1260, 1240, 1175, 1100, 1060, 1020, 975, 840, and 805 cm$^{-1}$;

(E) an ultraviolet absorption spectrum with the following absorption maxima:
  (a) in neutral methanol:

234 nm ($E^{1\%}_{1cm}$ = 147)

267 nm ($E^{1\%}_{1cm}$ = 74)

(b) in methanol containing 0.1 N HCl:

232 nm ($E^{1\%}_{1cm}$ = 132)

270 nm ($E^{1\%}_{1cm}$ = 76)

(c) in methanol containing 0.1 N NaOH:

250 nm ($E^{1\%}_{1cm}$ = 202)

~295 nm (shoulder)

(F) a specific rotation, $[\alpha]_D^{20}$, of $+50\pm4°$ (c=0.48, HCl N/100);

(G) the following $R_f$ values in paper chromatography on Whatman No. 1 paper, using *B. Subtilis* ATCC 6633 as a detection organism:

| Elution system (v:v:v) | $R_f$ value |
| --- | --- |
| (1) n-butanol saturated with Sörensen buffer pH 6.0 | 0.00 |
| (2) n-butanol saturated with water containing 2% of p-toluenesulfonic acid | 0.00 |
| (3) n-butanol saturated with water containing 2% of ammonium hydroxide | 0.00 |
| (4) Sörensen buffer, pH 6.0, saturated with n-butanol | 0.05 |
| (5) n-butanol:methanol:water 4:1:2 | 0.48 |
| (6) ethyl acetate saturated with water | 0.00 |
| (7) n-butanol:acetic acid:water 2:1:1 | 0.44 |

(H) the following $R_f$ values in the Silicagel thin-layer chromatographic systems indicated below:

| Elution system (v:v:v) | $R_f$ values |
| --- | --- |
| (1) aqueous 2.5% HCOONH$_4$:CH$_3$CN 65:35* | 0.32 |
| (2) n-butanol:acetic acid:water 4:2:5 | 0.80 |
| (3) n-butanol:acetic acid:water 4:2:5 | 0.52 |
| (4) n-propanol:n-butanol:1N NH$_4$OH | 0.12 |
| (5) n-butanol:acetic acid, water 4:1:5 | 0.15 |

1,2-on silanised Silicagel 60 F$_{254}$ plates
3,4,5-on Silicagel 60 F$_{254}$ plates
(*Internal standards: Caffeine R$_f$ 0.60; Cortisone R$_f$ 0.35; Dexamethasone R$_f$ 0.30);

(I) an amino-acid analysis, after acid hydrolysis in 6 N hydrochloric acid at 110° C. for 6 hours, which shows the presence of at least the following aminoacids: alanine, leucine, glycine, aspartic acid, phenylalanine, ornithine, p-hydroxyphenylglycine, and hydroxy, chloro-substituted phenylglycine;

(J) a carbohydrate analysis of the acid hydrolyzate after 2 hours in 2 N H$_2$SO$_4$ at 100° C. which indicates the presence of D-mannose;

(K) a retention time ($t_R$) of 6' 84/100" when analyzed by reverse phase HPLC using an octadecylsilanized silica gel column (3.9 mm ID×300 mm), and a mixture HCOONH$_4$ 0.025 M/CH$_3$CN 60/40 (v/v) as the mobile phase with a flow rate of 2 ml/min (internal standards: Anthracene $t_R$ 35' 18/100"; α-Nitronaphthalene $t_R$ 11' 14/100"; Toluene 8' 64/100").

* * * * *